United States Patent [19]

Lloyd

[11] Patent Number: 5,063,948
[45] Date of Patent: Nov. 12, 1991

[54] BRISTLED DENTAL FLOSS

[76] Inventor: O. H. Perry Lloyd, P.O. Box 3127, Jekyll Island, Ga. 31520

[21] Appl. No.: 508,271

[22] Filed: Apr. 11, 1990

[51] Int. Cl.⁵ .............................................. A61C 15/00
[52] U.S. Cl. ..................................... 132/321; 132/329
[58] Field of Search ............... 132/321, 329, 323, 324, 132/325, 326, 327, 328

[56] References Cited

U.S. PATENT DOCUMENTS

| | | | |
|---|---|---|---|
| 1,285,988 | 11/1918 | Gudebrod et al. | 132/323 |
| 1,989,895 | 2/1935 | Van Gilder | 132/323 |
| 2,522,794 | 9/1950 | Medof | 132/325 |
| 3,141,466 | 7/1964 | Fleming | 132/329 |
| 3,789,858 | 2/1974 | Pesce | 132/321 |
| 3,837,351 | 9/1974 | Thornton | 132/321 |
| 4,008,727 | 2/1977 | Thornton | 132/321 |
| 4,029,113 | 6/1977 | Guyton | 132/321 |
| 4,265,258 | 5/1981 | Eaton, II | 132/93 |
| 4,277,297 | 7/1981 | Thornton | 132/329 X |
| 4,450,849 | 5/1984 | Cerceo et al. | 132/89 |
| 4,523,600 | 6/1985 | Donovan | 132/321 |
| 4,836,226 | 6/1989 | Wolak | 132/89 |
| 4,911,187 | 3/1990 | Castillo | 132/321 |
| 4,922,936 | 5/1990 | Buzzi et al. | 132/329 |
| 4,924,811 | 5/1990 | Axelrod | 132/323 X |
| 4,974,615 | 12/1990 | Doundoulakis | 132/321 |

FOREIGN PATENT DOCUMENTS

| | | | |
|---|---|---|---|
| 2922824 | 12/1979 | Fed. Rep. of Germany | 132/323 |
| 3226129 | 1/1984 | Fed. Rep. of Germany | 132/323 |

*Primary Examiner*—Robert P. Swiatek
*Assistant Examiner*—Nicholas D. Lucchesi
*Attorney, Agent, or Firm*—Jeffrey A. Hall

[57] ABSTRACT

A bristled dental floss comprised of a plurality of sub-fibers each having a plurality of bristles secured thereto. The sub-fibers, bristles, or both, may be stiffened with wax, TEFLON, nylon, or like material. The bristled dental floss has improved cleaning and massaging ability facilitating the dislodging and removal of unwanted particles from the interproximal and gingival embrasive regions.

16 Claims, 2 Drawing Sheets

BRISTLED DENTAL FLOSS

BACKGROUND OF THE INVENTION

1. Field of the Invention

This invention relates to dental floss, in particular to dental floss having bristles or spines affixed substantially perpendicular to the longitudinal axis of the floss.

2. Description of Prior Art

Dental floss is a well known toilet article used to promote dental hygiene by aiding in the removal of particles lodged in the interproximal areas of the teeth. In its most standard use a segment of dental floss is passed between two adjacent teeth and manipulated therein to dislodge food and other unwanted particles caught between the teeth. Conventional floss is usually manipulated under tension against the tooth surface being cleaned in such a way that its motion is lateral to the longitudinal axis of the floss in an occlusogingival direction along the surface of the tooth. Such movement brings it into direct contact with the outstanding convex surfaces of the tooth from the crown to about the neck level of the tooth. That is to say, from the occlusive region, in the gingival direction to a line between the point at which the longitudinal contour of the tooth becomes perpendicular to the axis of the tension on the floss, and the highest most occlusiveward points of gum adhesion on the lateral faces of the tooth. This movement, if successful, mechanically dislodges particles of food, plaque, and other debris lodged on these surfaces, but does not reach into pockets of gum disattachment in the interproximal regions in the gingival direction from the above described line nor does it contact concave surfaces in the radial contour of the tooth.

A number of serious problems result from the use of conventional floss and flossing methods notwithstanding the benefits obtained from regular use. One serious disadvantage of conventional dental floss is the damage to the gum caused by forceful contact of the dental floss against the gum, which is both painful and often leads to bleeding from the gum. Gingival injury can result from this forceful manipulation where the stretched smooth floss under pressure cuts directly into the gum. If the gingival tissue is in a diseased or unhealthy state, it often swells, bleeds easily, and is hypersensitive to conventional dental floss and flossing action. Due to the significant prevalence of gum disease, and to the injurious nature of conventional dental floss, most users of dental floss would prefer a floss which is easy and convenient to use without the concommitant drawbacks of conventional floss.

Another significant disadvantage of prior art flosses is that no amount of tension or manipulation can bring such floss into contact with either the concave surfaces of the tooth's topography, or, with tooth surfaces in pockets of gum disattachment below, i.e. toward the root from the neck of the tooth, short of damaging the gum attachment to the lateral surfaces of the tooth. Furthermore, due to limitations in the surface topography of prior flosses there is little or no salutary massage to the gum surfaces surrounding the tooth, and provides only an inefficient means of transporting the dislodged particles from surfaces which it does contact.

Heretofore, a wide variety of dental flosses and floss-like articles have been proposed and implemented. Conventional dental flosses are generally composed of relatively small diameter filaments woven together into a single elongate strand. A number of attempts have been made to improve upon conventional floss. One attempted solution is illustrated in U.S. Pat. No. 4,265,258 issued to Eaton, Il. This dental floss consisted of a relatively large diameter dental floss having a multitude of fibers overlain upon each other and, in some cases, extending beyond the main body of the dental floss. Although such a configuration provided an alternative to conventional floss, such floss had significant problems and limitations associated therewith. A primary problem with this approach is that in a way similar to conventional floss, this overlain floss could not clean either concave surfaces of the tooth's topography or tooth surfaces in pockets of gum disattachment. Furthermore, this approach provided little improvement over conventional floss in the transport and removal of material which is successfully dislodged from the interproximal regions.

Another approach is illustrated in U.S. Pat. 4,450,849 issued to Cerceo et. al. in which a dental tape having rows of protuberances aligned obliquely to the parallel edges of the tape is disclosed. Such tape, although superior to conventional floss in plaque removal capabilities is significantly limited in its cleaning and removal capability of interproximal regions. As in the case of conventional floss and overlain floss, such dental tape could not adequately clean either concave surfaces on the tooth or surfaces of the tooth or gum below the level of the neck of the tooth.

A still different approach is shown in U.S. Pat. No. 4,836,226 issued to Wolak wherein an endless article for cleaning teeth is disclosed. Such endless article was stretchable and included an abrasive surface of either ribs or dimples. This attempted solution is inadequate due to the difficulty in providing such article with a sufficient cleaning and removal texture.

SUMMARY OF THE INVENTION

Accordingly I claim the following as the objects and advantages of my invention to provide a new and improved dental floss for easily, reliably, and efficiently removing plaque, food particles, and other unwanted material from the interproximal regions of the teeth and gums; to provide such a dental floss which removes plaque and other unwanted particles with greater efficiency than conventional floss; to provide such a floss which engages the teeth and gums with a larger surface area during cleaning and is provided with a multitude of bristles to engage, dislodge, and remove unwanted particles while providing an improved abrasive cleaning action, and to provide such a floss which, due to the arrangement of bristles thereon, can clean the interproximal tooth surfaces by lengthwise movement as well as side-to-side movement.

In addition, I claim the following additional objects and advantages: to provide a dental floss for removing tartar, cleaning away plaque, and dislodging and removing food particles that is extremely safe and versatile and economical to manufacture, and to provide such a floss requiring a minimum of dexterity in removing plaque, tartar, and food particles by movement in occlusal, buccal, and lingual directions.

To this end I have invented an improved dental floss having a multitude of projecting bristles or spines secured to a plurality of sub-fibers which, when woven or otherwise associated together, provide a bristled floss having improved mechanical cleaning properties. The bristles may be rigid or semirigid and project independently from the main or woven strand. The floss and bristles may be waxed or unwaxed, smooth or treated, and tasteful and aromatic additives may be incorporated within the sub-fibers and bristles. The bristles being self-supporting greatly increase the cleaning and removal capacity of the floss. Various orientations and spacings may be provided to facilitate acceptance and application to a broad spectrum of user preferences.

The bristles may be affixed and spaced upon an individual sub-fiber or upon some or all of those sub-fibers making up a strand by mechanical means, such as a wrap, loop, knot, or by chemical bonding followed by a coating of wax, TEFLON, nylon, polyester, or the like.

A plurality of sub-fibers may then be woven or otherwise intertwined to form a composite strand of floss. As the individual sub-fibers have bristles affixed thereto, by alternating the spacing and arrangement of the bristles on the sub-fiber a vast array of bristle spacing and arrangements can be readily produced. The bristles extend and magnify the cleaning and removal capabilities of floss and enable and facilitate the cleaning of concavities and pockets of gum disadhesion beyond the reach of conventional floss, physically projecting into such areas and thereby dislodging and removing unwanted material from them.

It is further contemplated that the bristled floss, drawn lengthwise, bucco-lingually, in a reciprocating motion impels the bristles in a direction perpendicular to their axis, thereby producing an efficient and effective removal mechanism of particles, plaque, and tartar from the interproximal area. Moreover, the bristles provide a healthy and stimulating massage of the gum surfaces while simultaneously cleaning and toning them.

Additionally, by assembling a plurality of sub-fibers with bristles attached thereto together into a bristled floss strand a number of novel results may be achieved. For example, if the sub-fibers are selectively stiffened or otherwise rigidified, the bristled floss becomes pushable, and when the bristled floss is severed in an inter-bristle segment, a means is provided of inserting the severed end endwise into a space otherwise inaccessible due to the proximity of adjoining teeth or the impeding structure of a dental article. Various arrangements of the bristles are possible with this assemblage of bristled sub-fibers, and it is contemplated that a wide variety of shapes and lengths of bristles, either interspersed, graduated, or both, may be utilized.

Readers will find further objects and advantages of the invention from a consideration of the ensuing description and accompanying drawings.

DETAILED DESCRIPTION OF A PREFERRED EMBODIMENT

Figure 1:
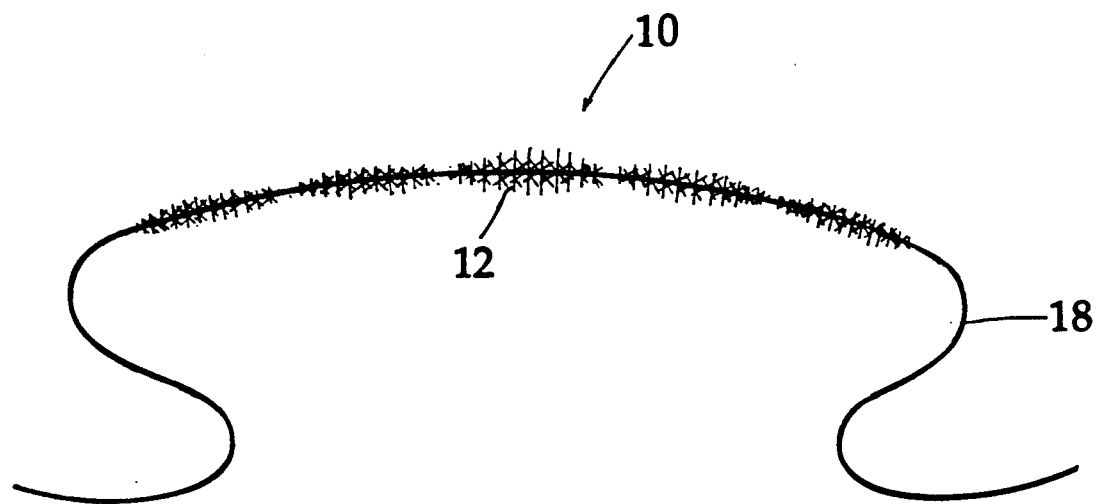
FIG. 1 shows a front perspective view of a bristled dental floss assembled according to the preferred embodiment of the invention.
Figure 2:
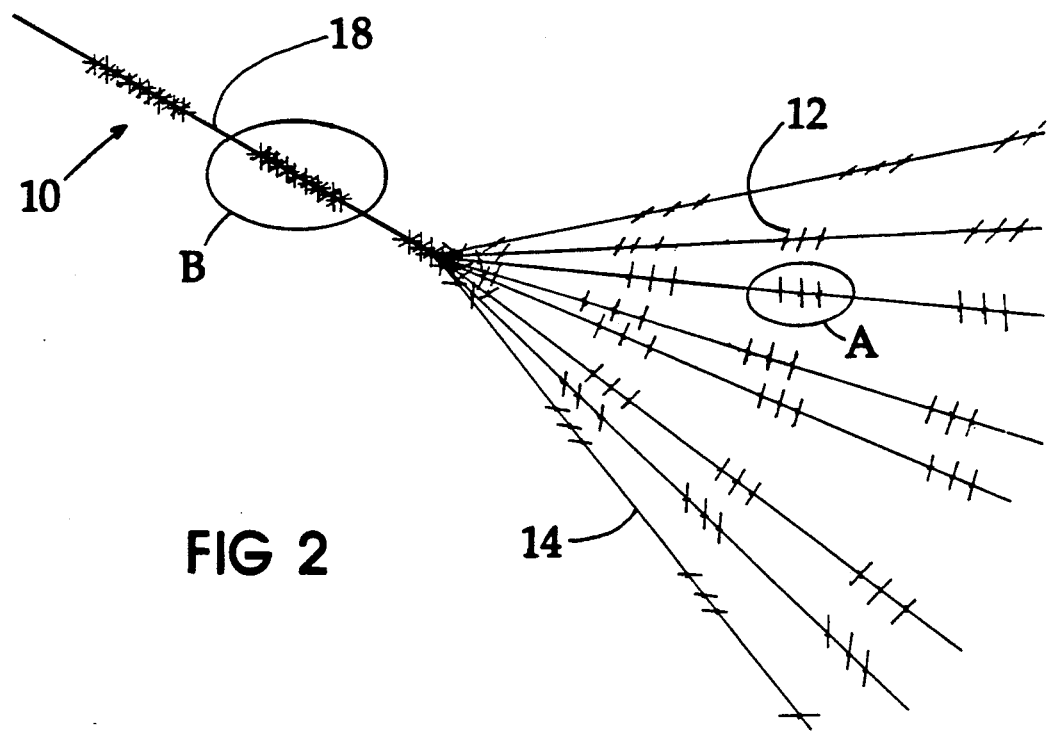
FIG. 2 shows a front perspective view of a bristled dental floss showing a plurality of sub-fibers both assembled and independent according to the invention.

FIG. 1 shows a bristled dental floss 10 according to the preferred embodiment of the invention. The bristled floss is comprised of a plurality of bristles 12 attached to a floss strand 18. FIG. 2 also shows a bristled dental floss according to the preferred embodiment of the invention. The bristled floss is comprised of a plurality of sub-fibers 14 having a plurality of bristles 12 attached to a sub-fiber unit by securing knot 16. The sub-fibers 14 are then assembled together into bristled dental floss 10. In the preferred embodiment the assembly of sub-fibers are then dipped in either a wax, TEFLON, nylon or similar fixing agent. Bristles 12 may likewise be stiffened by dipping, spraying, or painting wax, TEFLON, or the like thereon. Sub-fibers 14 may be woven or otherwise entwined to form dental floss 10.

The sub-fibers 14 on which bristles 12 are affixed is preferably from 0.1 to 10 denier and the assembled floss strand is preferably between 0.03 to 0.00005 inches in thickness, and from 0.03 to 0.5 inches in width, but may be otherwise. The floss strand 18, in the preferred embodiment is filament yarn, but may be composed of polymeric film or other flexible material.

Figure 3:
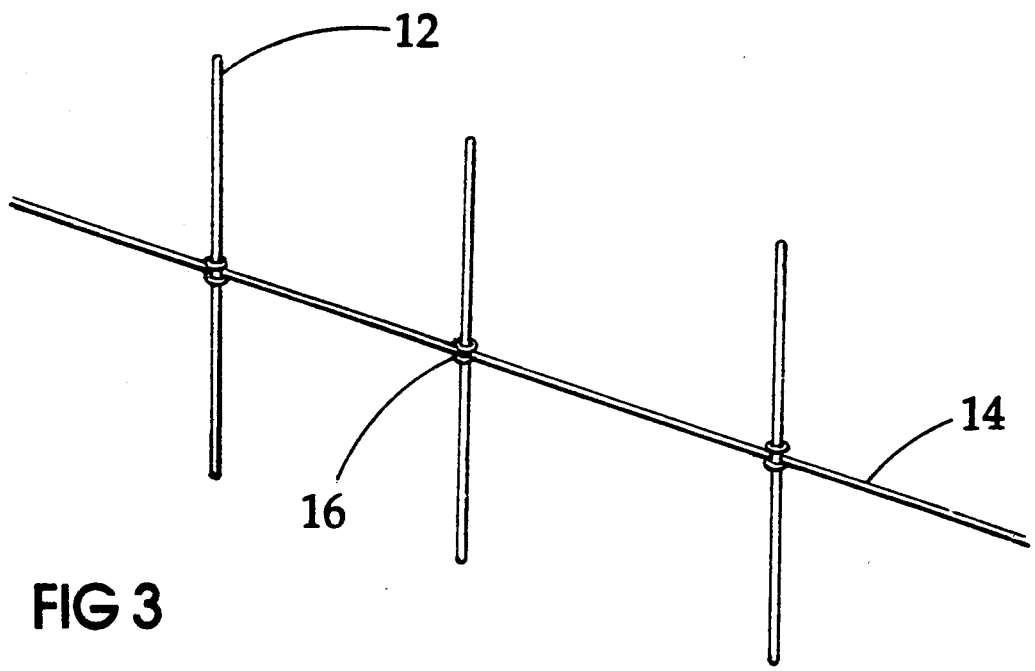
FIG. 3 shows an enlarged view A of bristles attached to an individual sub-fiber according to the invention.

Bristles 12 are preferably from approximately ⅛ to ⅜ inches in length and composed of a monofilament or multi-filament polymeric fiber, of which the filament or filaments are sufficiently rigid to be self-supporting. FIG. 3 shows an enlarged view of bristles 12 entwined in subfiber 14. In another embodiment a plurality of bristles 12 or spines may be affixed to a membranous or other filmtype substrate and by insertion through the substrate so as to protrude from both sides thereof, are then secured thereto by a thermal weld or chemical bonding well known in the art.

Figure 4:
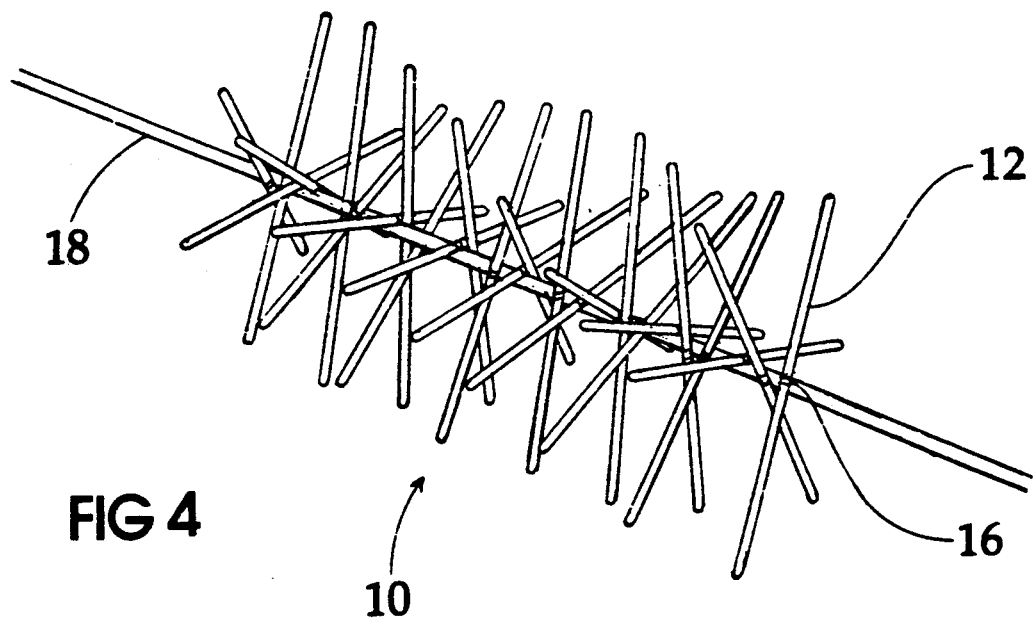
FIG. 4 shows an enlarged top perspective view B of the bristled floss showing a non-continuous bristle arrangement.

FIGS. 3-4 illustrate the attachment of bristles 12 to sub-fibers 14, and the association of sub-fibers 14 with one another. FIG. 3 shows an individual sub-fiber 14, preferably with a weight of about 0.1 to 10 denier knotted around an individual bristle 12. Although other weight sub-fibers and other attachment means are within the scope of the invention this configuration is preferred. The bristles 12 may be indented circumferentially or otherwise textured in order to provide a superior grip to sub-fiber 14 and a superior abrasive cleaning action.

Securing knot 16 is, in the preferred embodiment, a hitch type knot, preferably a clove hitch as shown in FIG. 3. Although other knots are well within the scope of the invention the clove hitch provides a simple, efficient, and secure means of attaching a bristle in the midst of a continuous fiber without necessitating the involvement of an end of the fiber.

FIGS. 1, 2 and 4 show how a great number of bristle distribution patterns and length configurations may be easily achieved using the method of assembly of multiple bristled sub-fibers woven or otherwise entwined together. For example, the entire strand of floss may be bristles. Alternatively, certain spaced portions may be left without bristles or populated with either a greater or lesser density of bristles of a greater or lesser length or stiffness as desired. Segments of the entwined sub-fibers may be selectively hardened or rigidified with wax, TEFLON, nylon, or the like. If such hardened floss is severed it may then be inserted lengthwise into spaces between the teeth and gums which would be otherwise inaccessible to the floss.

In the use of the present invention, a segment of bristled floss 10 is caused to pass through the space between two adjacent teeth by exerting a force on the ends of the segment directed toward the gum or interproximal area. Preferably, differential force is applied as the bristled floss is shifted alternatively within the space between the teeth until the floss is disposed in the interproximal area. The floss may then be gently manipulated down to the gingival sulcus, situated between the tooth and the gum tissue. Either an occluso-gingival motion or a bucco-lingual motion is then used. As the bristled floss 10 is so manipulated between the teeth a wide variety of teeth cleaning and gum massage functions are effectuated, including cleansing, scouring, massage, removal of particles, plaque, tartar, etc. As is readily apparent bristles 12 in conjunction with the floss strand 10 greatly facilitate the removal of unwanted particles from the teeth and gums. When the gingival sulcus and the tooth surfaces have been cleaned in this manner, the floss is then removed by either pulling the floss completely through the interproximal space, or by passing the floss between the crowns of the teeth. Remaining particles of loosened matter may then be removed by rinsing with a mouth rinse or water.

While the above description contains many specificities, the reader should not construe these as limitations on the scope of the invention, but merely as exemplifications of preferred embodiments thereof. Those skilled in the art will envision many other possible variations are within its scope. For example, skilled artisans will readily be able to change the dimensions and shapes of the various embodiments. They will be able to make the sub-fibers and bristles out of alternative synthetic or natural materials. They can substitute alternative bristle attachment means such as various knots, chemical agents, or thermal or laser welding techniques, and still fall within the scope of this invention. Accordingly, the reader is requested to determine the scope of the invention by the appended claims and their legal equivalents rather than the examples which have been given.

I claim:
1. A dental floss comprising:
   a plurality of sub-fibers secured together into a self supporting strand, and
   a plurality of self supporting bristles, said bristles are individually attached to each of said sub fibers by a knot.
2. The bristled floss of claim 1 wherein said knot is a clove hitch.
3. The bristled floss of claim 1 wherein said sub-fibers are stiffened with a wax.
4. The bristled floss of claim 1 wherein said bristles are stiffened with a wax.
5. The bristled floss of claim 1 wherein said sub-fibers are stiffened with TEFLON.
6. The bristled floss of claim 1 wherein said bristles are stiffened with TEFLON.
7. The bristled floss of claim 1 wherein said sub-fibers are stiffened with a nylon.
8. The bristled floss of claim 1 wherein said bristles are stiffened with a nylon.
9. A bristled dental floss comprising a strand of a plurality of sub-fibers associated with one another, said sub-fibers each having a plurality of bristles independently secured thereto, and each of said bristles is individually attached to individual sub-fibers by a knot.
10. The bristled floss of claim 9 wherein said knot is a clove hitch.
11. The bristled floss of claim 9 wherein said sub-fibers are stiffened with a wax.
12. The bristled floss of claim 9 wherein said bristles are stiffened with a wax.
13. The bristled floss of claim 9 wherein said sub-fibers are stiffened with TEFLON.
14. The bristled floss of claim 9 wherein said bristles are stiffened with TEFLON.
15. The bristled floss of claim 9 wherein said sub-fibers are stiffened with a nylon.
16. The bristled floss of claim 9 wherein said bristles are stiffened with a nylon.

* * * * *